United States Patent
Glasner et al.

(10) Patent No.: US 11,461,920 B2
(45) Date of Patent: Oct. 4, 2022

(54) APPARATUS AND METHOD FOR OBJECT RECOGNITION

(71) Applicant: AIC Innovations Group, Inc., New York, NY (US)

(72) Inventors: Daniel Glasner, New York, NY (US); Lei Guan, Jersey City, NJ (US); Adam Hanina, New York, NY (US); Li Zhang, Princeton, NJ (US)

(73) Assignee: AIC Innovations Group, Inc., New York, NY (US)

( * ) Notice: Subject to any disclaimer, the term of this patent is extended or adjusted under 35 U.S.C. 154(b) by 65 days.

(21) Appl. No.: 16/879,215

(22) Filed: May 20, 2020

(65) Prior Publication Data

US 2020/0357130 A1    Nov. 12, 2020

Related U.S. Application Data

(63) Continuation of application No. 15/887,775, filed on Feb. 2, 2018, now Pat. No. 10,664,987.

(51) Int. Cl.
*A61B 5/00*     (2006.01)
*G06K 9/62*    (2022.01)
(Continued)

(52) U.S. Cl.
CPC ............. *G06T 7/70* (2017.01); *A61B 5/4833* (2013.01); *G06K 9/6215* (2013.01);
(Continued)

(58) Field of Classification Search
CPC ........ G06V 10/44; G06V 10/56; G06V 10/82; G06V 30/194
See application file for complete search history.

(56) References Cited

U.S. PATENT DOCUMENTS 6,610,973 B1 *   8/2003   Davis, III ................. A61J 7/02
                                                  250/222.1
7,991,507 B2 *   8/2011   Liff ....................... G06Q 10/087
                                                  221/13
(Continued)

OTHER PUBLICATIONS

EP Extended European Search Report in European Appln. No. 19746767.3, dated Feb. 17, 2021, 12 pages.
(Continued)

*Primary Examiner* — Soo Shin
(74) *Attorney, Agent, or Firm* — Fish & Richardson P.C.

(57) ABSTRACT

A system and method for recognizing an object. The system includes an imaging apparatus for capturing an image of an object and a processor for receiving the captured image of the object, and for, when it is determined that fewer than a predetermined number of objects have been previously imaged, for determining whether the image of the captured object includes one or more characteristics determined to be similar to a same characteristic in a group of previously imaged objects so that the captured image is grouped with the previously imaged objects, or whether the image of the captured object includes one or more characteristics determined to be dissimilar to a same characteristic in a group of previously imaged objects so that the captured image is not grouped with the previously imaged objects, and the image of the captured object starts another group of previously imaged objects.

19 Claims, 4 Drawing Sheets

(51) Int. Cl.
*G06T 7/70* (2017.01)
*G06V 10/44* (2022.01)
*G06V 10/56* (2022.01)
*G06V 10/82* (2022.01)
*G06V 30/194* (2022.01)

(52) U.S. Cl.
CPC ........... *G06K 9/6271* (2013.01); *G06V 10/44* (2022.01); *G06V 10/56* (2022.01); *G06V 30/194* (2022.01)

(56) References Cited

U.S. PATENT DOCUMENTS

| | | | |
|---|---|---|---|
| 7,995,831 B2 * | 8/2011 | Eller | G16H 20/13 |
| | | | 382/142 |
| 8,538,775 B2 | 9/2013 | Skomra | |
| 8,666,781 B2 | 3/2014 | Hanina et al. | |
| 8,731,961 B2 | 5/2014 | Hanina et al. | |
| 8,781,856 B2 | 7/2014 | Hanina et al. | |
| 8,861,816 B2 * | 10/2014 | Lang | G06K 9/6293 |
| | | | 382/128 |
| 9,183,601 B2 | 11/2015 | Hanina et al. | |
| 9,256,776 B2 | 2/2016 | Hanina et al. | |
| 9,293,060 B2 | 3/2016 | Hanina et al. | |
| 9,400,909 B2 * | 7/2016 | Hanina | G06K 7/1408 |
| 9,406,127 B2 * | 8/2016 | Helgason | G06V 20/66 |
| 9,824,297 B1 * | 11/2017 | Guan | G16H 40/20 |
| 9,883,786 B2 * | 2/2018 | Hanina | G09B 19/00 |
| 2011/0119073 A1 | 5/2011 | Hanina et al. | |
| 2011/0153360 A1 | 6/2011 | Hanina et al. | |
| 2012/0009555 A1 * | 1/2012 | Hanina | G16H 20/17 |
| | | | 434/262 |
| 2012/0084091 A1 * | 4/2012 | Hanina | G06Q 99/00 |
| | | | 705/2 |
| 2012/0199239 A1 | 9/2012 | Okuda et al. | |
| 2012/0316897 A1 | 12/2012 | Hanina et al. | |
| 2013/0142406 A1 | 6/2013 | Lang | |
| 2014/0169673 A1 | 6/2014 | Liu et al. | |
| 2014/0233788 A1 | 8/2014 | Fox et al. | |
| 2014/0263389 A1 | 9/2014 | Perozek et al. | |
| 2015/0278224 A1 * | 10/2015 | Jaber | G06F 16/583 |
| | | | 707/758 |
| 2020/0357130 A1 * | 11/2020 | Glasner | G06K 9/6215 |
| 2022/0040414 A1 * | 2/2022 | Sjolund | A61B 5/7455 |

OTHER PUBLICATIONS

Young et al., "A Fast and Stable Incremental Clustering Algorithm," 2010 Seventh International Conference on Information Technology: New Generations, Apr. 2010, 204-209.

PCT International Preliminary Report in Patentability in International Appln. No. PCT/US2019/013641, dated Aug. 4, 2020, 7 pages.

International Search Report and Written Opinion for Intl App No. PCT/US2019/13641, dated Apr. 22, 2019 (8 pages).

* cited by examiner

APPARATUS AND METHOD FOR OBJECT RECOGNITION

CROSS-REFERENCE TO RELATED APPLICATIONS

This application claims priority to U.S. application Ser. No. 15/887,775, filed Feb. 2, 2018, the contents of which are incorporated herein by reference in their entirety.

FIELD

This disclosure relates generally to the visual recognition of an object, such as a medication pill or other medication form, and more particularly to an apparatus and method for medication recognition for use with a medication monitoring system employing video capture, allowing for a diverse set of medication to be recognized with no initial visual training of the system required for each medication.

BACKGROUND

U.S. patent application Ser. No. 11/839,723, filed Aug. 16, 2007, titled Mobile Wireless Medication Management System provides a medication management system employing mobile devices and an imaging technology so that a user is able to show a pill to be taken to the system, and the system can then identify the medication. Patient histories are available to an administrator, including various vital signs as measured by the system. Images may also be taken of the patient, provider, medication container or the like. While the system professes to ensure adherence to a protocol, the system only provides such help if requested by a user. There is in fact no particular manner in which to ensure actual adherence or ingestion of the medication, or the relationship of adherence to the efficacy or safety of the drug over time. When requiring adherence to a predetermined protocol for a clinical trial, this is particularly relevant. Similarly, there is no mention of non-pill based medications. Furthermore, there is an assumption that a medication has been already trained to be recognized by the system, an assumption that may cause a problem given the number of different possible medications, including generic medications, that may be taken by an individual in accordance with a particular prescription.

The inventors of the present invention have determined that prior art systems fail to describe the recognition of a previously untrained medication by a medication system.

Therefore, it would be desirable to provide an apparatus that overcomes the drawbacks of the prior art.

SUMMARY

In U.S. patent application Ser. No. 12/620,686, filed Nov. 18, 2009, titled Method and Apparatus for Verification of Medication Administration Adherence, abandoned; U.S. patent application Ser. No. 13/558,377, filed Jul. 26, 2012, titled Method and Apparatus or Verification of Medication Administration Adherence, now U.S. Pat. No. 8,781,856; U.S. patent application Ser. No. 12/646,383, filed Dec. 23, 2009, titled Method and Apparatus for Verification of Clinical Trial Adherence, abandoned; U.S. patent application Ser. No. 13/558,380, filed Jul. 26, 2012, titled Method and Apparatus for Verification of Clinical Trial Adherence, now U.S. Pat. No. 8,731,961; U.S. patent application Ser. No. 12/646,603, filed Dec. 23, 2009, titled Method and Apparatus for Management of Clinical Trials, Now U.S. Pat. No. 8,666,781; U.S. patent application Ser. No. 12/728,721, filed Mar. 22, 2010, titled Apparatus and Method for Collection of Protocol Adherence Data, now U.S. Pat. No. 9,183,601; U.S. patent application Ser. No. 12/815,037, filed Jun. 14, 2010, titled Apparatus and Method for Recognition of Patient Activities when Obtaining Protocol Adherence Data, now U.S. Pat. No. 9,293,060; U.S. patent application Ser. No. 13/189,518, filed Jul. 24, 2011, titled Method and Apparatus for Monitoring Medication Adherence, currently pending; U.S. patent application Ser. No. 13/235,387, filed Sep. 18, 2011, titled Apparatus and Method for Recognition of Patient Activities, currently pending; U.S. patent application Ser. No. 13/674,209, filed Nov. 12, 2012, titled Method and Apparatus for Identification, now U.S. Pat. No. 9,256,776; and U.S. patent application Ser. No. 13/674,459, filed Nov. 12, 2012, titled Method and Apparatus for Recognition of Inhaler Actuation, currently pending; the contents of these applications being incorporated herein by reference, the inventors of the present invention have proposed a system, method and apparatus that allow for complete control and verification of adherence to a prescribed medication protocol or machine or apparatus use in a clinical trial or disease management setting, whether in a health care provider's care, or when self-administered in a homecare situation by a patient.

The inventive solution, in accordance with one or more embodiments of the present invention, recognizes the need to be able to apply the above described system in a great number of scenarios where knowledge of the visual characteristics of the medication to be taken, or other medical or other object to be recognized, may not be known, or where the number of medications to be monitored by the system may be very large, and where no special hardware is to be employed in the system calibration process, or during use in the medication recognition process, such as a color chart, special tray or medication holder or the like. In accordance with one or more embodiments of the present invention, one or more users of the system may be first encouraged to present a particular medication or other object to the system, preferably in the presence of an individual who can confirm that the medication or object is the expected medication or object, or in accordance with another acceptable method for confirming that the presented medication or object is the correct medication or object, such as through application of a bar code or other identifying characteristic. The presented object or medication is then preferably imaged by the system and stored as a base image for the expected medication or object.

Subsequent use of the system to confirm proper medication administration encourages the user to similarly present the next to be taken medication or other object to an imaging device, where still or video images of the medication or object are captured. An initial determination is made as to whether the system is able to confirm that the newly-captured image includes a medication or other object that is the same as that in the base medication or object, or is a different medication. In accordance with embodiments of the invention, the base medication or object may be modified by one or more transfer functions, to account for possible changes in ambient light, etc., to confirm it the newly presented medication or object is the same as the base medication or object.

If it is determined that the newly imaged medication or object is not the same as the base medication or object, an alert may be provided to the user, or to a healthcare provider that the incorrect medication has been presented. To the user, such alert may comprise a notice to the user that the medication is incorrect, and a presentation of further instructions for the user to present the proper medication. If it is determined that the newly imaged medication or object is the same as the base medication or object, the user may then be prompted to next administer or ingest the medication. Additionally, the images or video of the newly imaged medication or object is preferably grouped with the base medication, thus expanding the number of samples of the base medication available for use in confirming the proper identity of future imaged medication or objects.

The described process may continue until a predetermined number of confirmed imaged medications or objects are collected, or until some other measure of a sufficient number of images having been collected is confirmed, such as by testing whether the collected images cover a sufficient number of lighting scenarios, for example. Once confirmed, the collected images may be processed through a visual learning system, such as through a supervised or unsupervised learning system, to provide a more robust model of the base medication, thus providing an enhanced recognition platform for the future recognition of medication or other objects. This process may be completed multiple times, as increased numbers of collected images, when processed as part of a learning system, will improve the accuracy of the system.

The learning systems preferably focus on a number of consistently-recognizable characteristics of the medication or object. These characteristics may be defined in any number of dimensions, and may include color, shape, surface reflectivity, surface markings, relationship between any number of these characteristics, etc.

Various medications or objects may then be trained so that the system is adapted to recognize and differentiate between these various medications or objects. Once trained, if a user is prescribed one of the trained medications, the system will recognize whether the user presents the prescribed medication to the system (as noted in one or more of the above-note applications). If, however, a medication is prescribed that has not been trained into the system, or if the user is to take a generic medication having a yet unknown set of visual characteristics, the noted process may be employed to allow the system to operate in the absence of any prior training of the particular medication or object.

In addition to simply imaging the medication or object during use of the system by a standard user, the user may instead be asked to perform a mini-training process with the system. The user may be asked to show the medication or object to an imaging camera of the system in a predetermined sequence. The user may also be asked to perform a particular gesture or set of gestures or predetermined steps with the medication. The system may turn on lights, or provide illumination from the display of the imaging device, etc. at different times of the mini-training process. Such lights or other illumination may be employed to change the illumination of a medication or environment, or may be used to change a color of the environment, either alone or in sequence, to aid in a more accurate calibration and/or identification process. Use of such a mini-training process increases the number of images available for use as the "base medication" and allows for faster training of the system.

Therefore, a method and system are provided allowing for proper identification of medication without the need for exhaustive training of each and every medication to be recognized.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which.

DETAILED DESCRIPTION

Information Capture System

Figure 1:
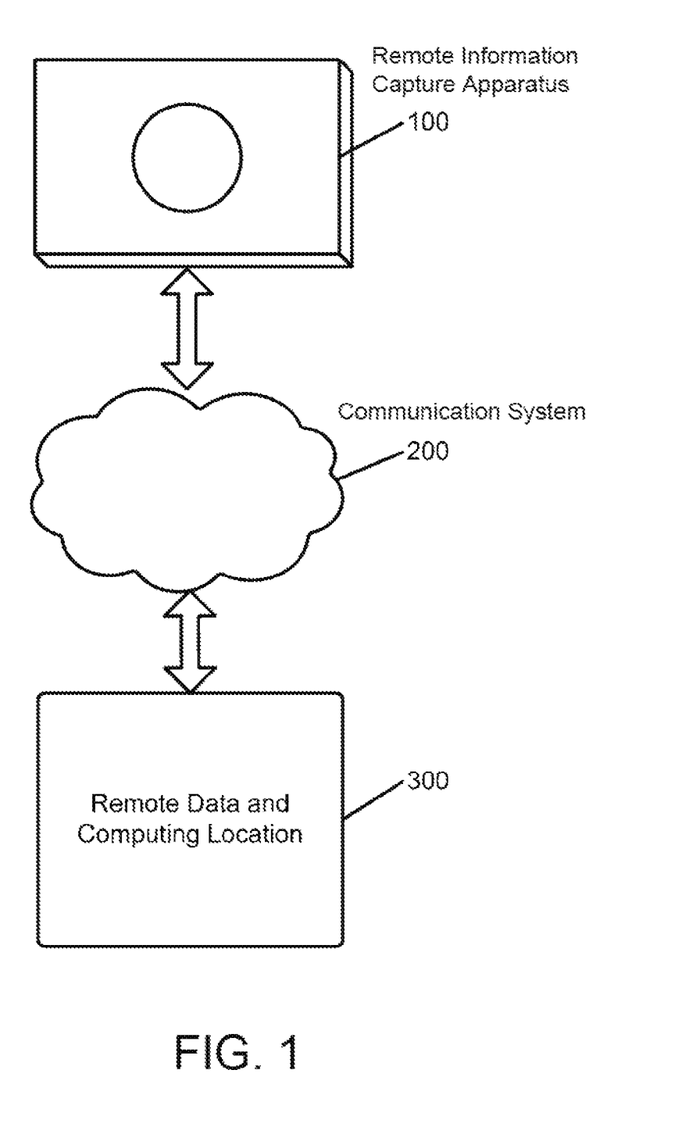
FIG. 1 depicts a data capture and transfer system constructed in accordance with an embodiment of the invention.

Referring first to FIG. 1, a data capture and transfer system constructed in accordance with an embodiment of the invention is shown. In FIG. 1, a remote information capture apparatus 100 is shown. Such apparatus is adapted to allow for the capture and processing of information in order to implement the system and method in accordance with the present invention, such as capturing one or more images of medication or other objects. Such information capture apparatus 100 is preferably placed in communication with a remote data and computing location 300 via a communication system 200, preferably the Internet or other communication system. Via communication system 200, information captured by apparatus 100 may be transmitted to remote data and computing location 300, and analysis information or other instructions may be provided from remote data and computing location 300 to apparatus 100. It is further contemplated that a plurality of such information capture apparatuses 100 may be coordinated to monitor a larger space than a space that can be covered by a single such apparatus. Thus, the apparatuses can be made aware of the presence of the other apparatuses, and may operate by transmitting all information to one of the apparatuses 100, or these apparatuses may each independently communicate with remote data and computing location, which is adapted to piece together the various information received from the plurality of devices 100. Remote system 300 may also comprise a data storage repository, or may be omitted, so that all processing is performed on capture apparatus 100.

The system may preferably process information at remote system 300 housing a database of collected information. New images acquired by an image acquisition camera 1110 (see FIG. 2) in local mobile device 100 may be transmitted to the remote location 300, one or more of the above-noted identification or processing techniques may be applied, and then the results of such analysis may be provided as feedback to a user or other healthcare provider to provide feedback to the user via device 100, or through another predefined communication method, such as by a registered mobile device number, text message, or other available communication system, to confirm that a medication presented to the system is a proper or improper medication.

Figure 2:
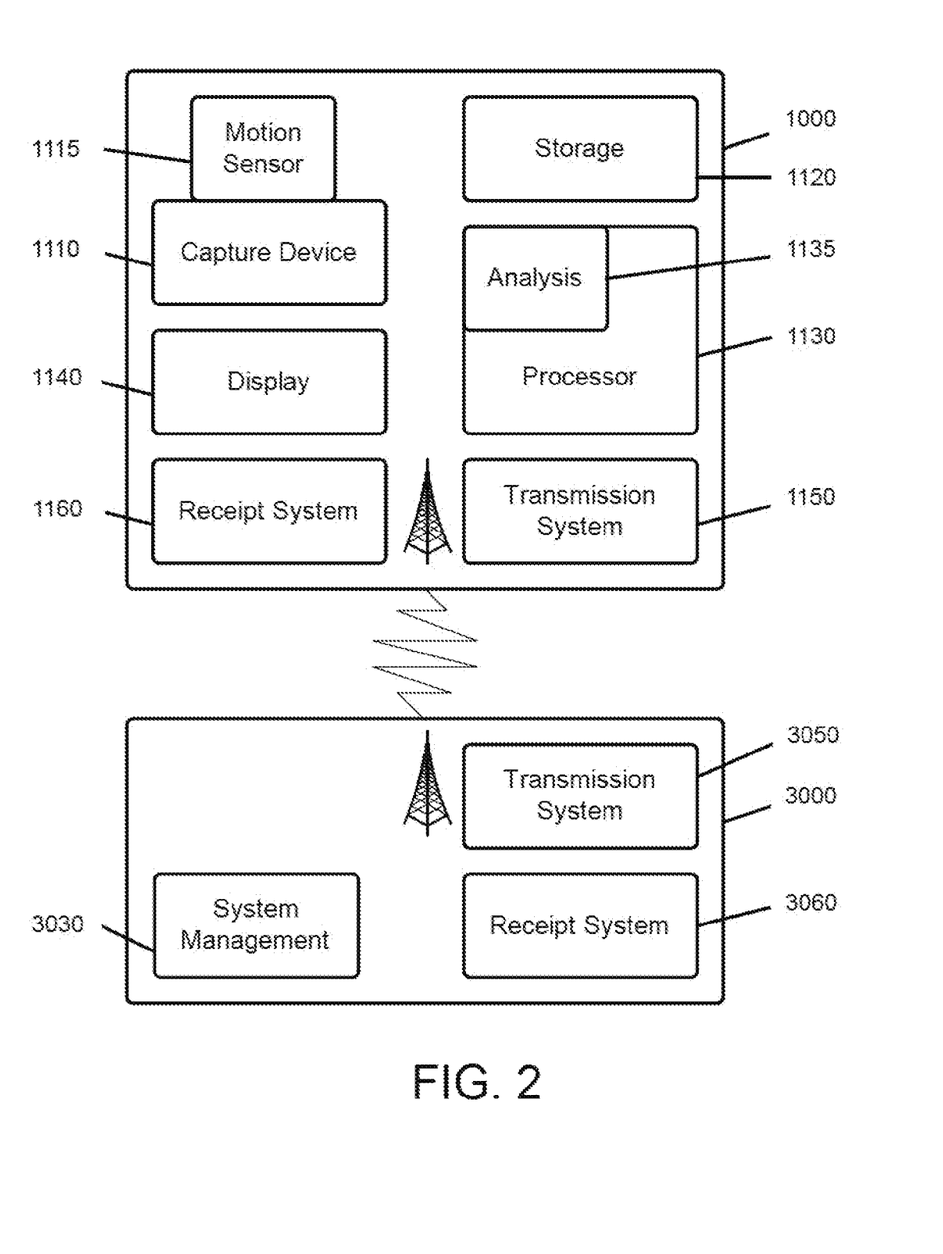
FIG. 2 depicts more detailed elements of the data capture and transfer system of FIG. 1.

Referring next to FIG. 2, a more detailed view of a preferred embodiment of remote information capture apparatus 1000 (as an example of apparatus 100) and remote data and computing location 3000 (as an example of location 300). As is shown in FIG. 2, apparatus 1000 comprises an information capture device 1110 for capturing video and audio data as desired. A motion detector 1115 or other appropriate trigger device may be provided (or may be omitted) associated with capture device 1110 to allow for the initiation and completion of data capture. Information capture device 1110 may comprise a visual data capture device, such as a visual camera, or may be provided with an infrared, night vision, 2D, 3D, distance camera, or other appropriate information capture device. A storage location 1120 is further provided for storing captured information, and a processor 1130 is provided to control such capture and storage, as well as other functions associated with the operation of remote information capture apparatus 1000. An analysis module 1135 is provided in accordance with processor 1130 to perform a portion of analysis of any captured information at the remote information capture apparatus 1000. Apparatus 1000 is further provided with a display 1140, and a data transmission and receipt system 1150 and 1160 for displaying information, and for communicating with remote data and computing location 3000. Remote data and computing location 3000 comprises system management functions 3030, and a transmission and reception system 3050 and 3060 for communicating with apparatus 1000. Transmission and reception system 3050 and 3060 may further comprise various GPS modules so that a location of the device can be determined at any time, and may further allow for a message to be sent to one or more individual apparatuses, broadcast to all apparatuses in a particular trial, or being used for administration of a particular prescription regimen, of broadcast to all available apparatuses.

In accordance with an embodiment of the invention, apparatus 1000 is preferably adapted to be part of a system that improves adherence to a medical protocol, and preferably may be employed in order to train the system to recognize visual characteristics of medication to be ingested by a user. Users of apparatus 1000 in accordance with this system give the system a tangible and concrete manner in which to train the system to recognize new medication to be later recognized by the system to confirm adherence. Apparatus 1000 of the invention is adapted to receive instructions for patients from remote data and computing location 3000 and provide these instructions to patients. Such instructions may comprise written, audio or audio instructions for guiding a user to perform one or more activities, such as performing a sequence of actions to allow a user to present a new medication to the system for training, or whether a user is adhering to a prescribed medication protocol by presenting a correct medication to the system.

The system, in accordance with an embodiment of the invention, is also applicable to monitoring of patient activities when being requested to perform particular actions, or when performing routine actions not specifically requested. Therefore, in accordance with an embodiment of the present invention, a method and apparatus may be provided for analyzing captured patient motion data, preferably in near real time to provide feedback to the user, to determine a number of times a participant performs some action that is, for example, considered suspicious, to determine one or more elements of diagnosing or monitoring disease, or to confirm proper positioning and processing of a new medication to be recognized by the system.

Figure 3:
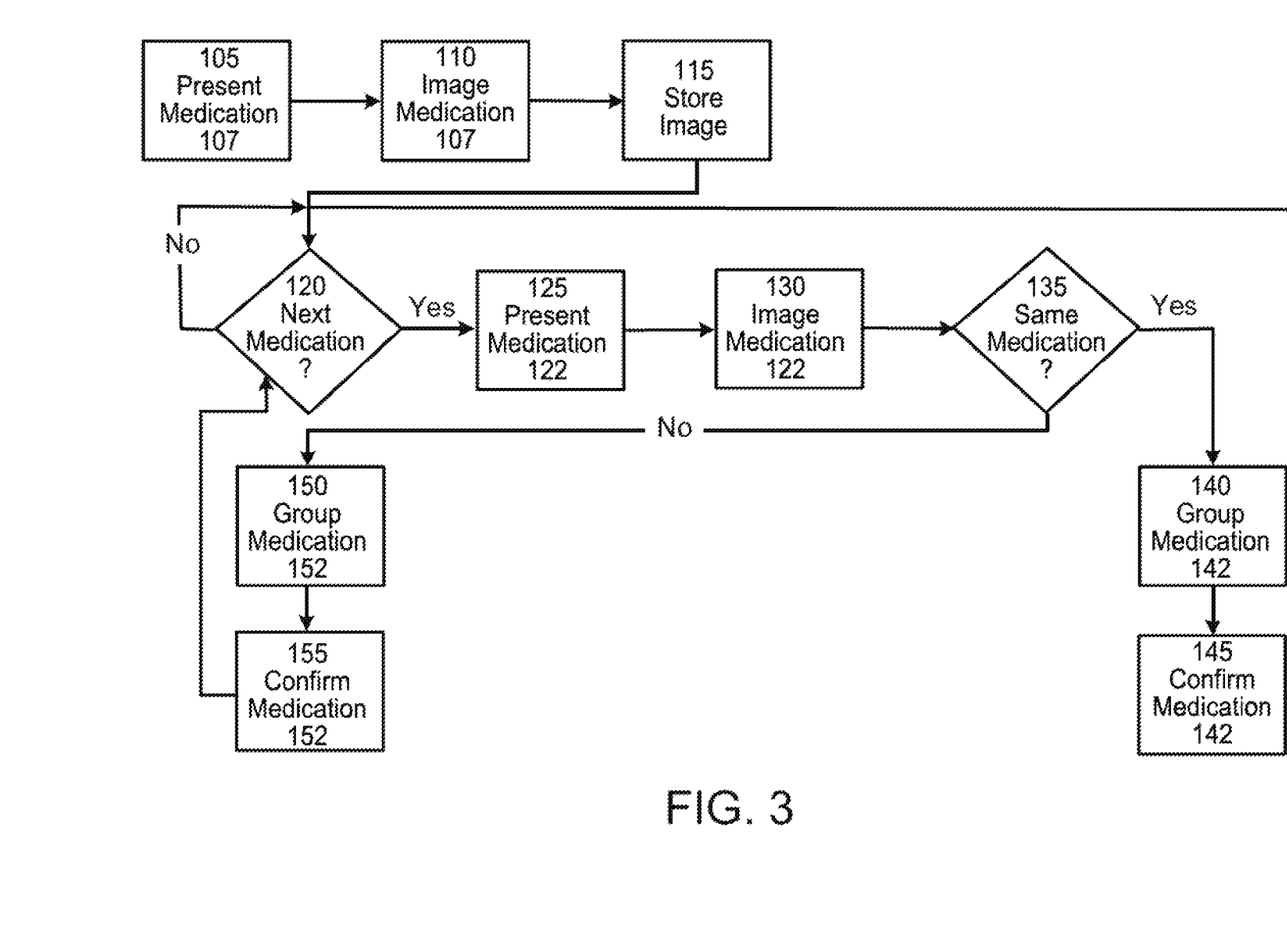
FIG. 3 is a flowchart diagram depicting a method for training a visual system during use to properly recognize a medication or other object employing a data capture and transfer system such as that depicted in FIGS. 1 and 2 in accordance with an embodiment of the invention.

Referring next to FIG. 3, and in accordance with an embodiment of the present invention depicting a method for use with the described system for initially training one or more medications by the system, at step 105, one or more users of the system may be first encouraged to present a particular medication or other object 107 to the system, preferably in the presence of an individual who can confirm that the medication or object is the expected medication or object, or in accordance with another acceptable method for confirming that the presented medication or object is the correct medication or object, such as through application of a bar code, label, or other identifying characteristic. The presented object or medication is then preferably imaged by the system at step 110 and stored as a base image for the expected medication or object at step 115. Imaging may take place using a camera included in a standard mobile device, and may comprise a conventional 2D camera, a 3D camera that can measure distance from the position of the camera, or other more complex visual sensors, such as infrared cameras and the like. Such distance measurements, 3D imaging and the like may allow for the use of size as a characteristic to be considered. Additionally, color calibration techniques may be employed to make sure that multiple different imaging devices are able to provide images with consistent colorings, thus improving the ability to recognize matching images.

Subsequent use of the system at step 120 sets the system to await input of a next medication 122. If no next medication 122 is presented to the system, processing continues at step 120 until a next medication is presented. If on the other hand, a next medication is presented at step 120, processing then passes to step 125 where the next medication is presented to the system, preferably in accordance with one or more guidance items on a display of the imaging device. The next medication 122 is imaged at step 130, and at step 135, an initial determination is made as to whether the imaged next medication 122 is the same or different that the prior medication 107. If the inquiry at step 135 is answered in the affirmative, and it is determined that the medication 122 is the same as medication 107, then at step 140 a medication group 142 is formed comprising the two medications 107, 122. After confirming the medication group at step 145, processing returns to step 120 to await presentation of a next medication.

If on the other hand the inquiry at step 135 is answered in the negative, and it is therefore determined that the medication 122 is not the same as medication 107, then processing passes to step 150 and a new group of medication 152 is formed, starting with medication 122. The group 152 is then confirmed at step 155, and processing returns to step 120 waiting for presentation of a next medication. For each additional medication presented, this process is performed, noting that the number of groups of medications 142 will continue to grow if new medications are introduced (each new medication group 152 becomes one of the grouped medications 142 in the next round). This process continues until a predetermined or otherwise sufficient number of medications are properly presented.

Figure 4:
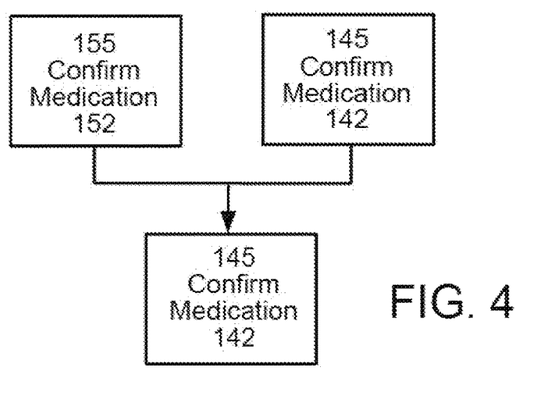
FIG. 4 is a flowchart diagram depicting a combining method in accordance with an embodiment of the invention.

As medications are presented, it is possible that two groups of medications may join together. This may happen if a same medication presented multiple times in different light, for example, were first put into different groups, but as additional medications are presented and imaged, various images "fill the gap" between the two groups, and the groups join together. This process is performed as shown in FIG. 4. As is shown in FIG. 4, after processing in accordance with FIG. 3 is completed, the system may have two or more medication groups 142, 152. As is shown in FIG. 4, a determination is preferably made between each group 142, 152 as to whether upon inclusion of additional medication images therein, whether the medication elements of each group overlap sufficiently to be considered a single group. Such combination method may include a least squares method or other known method for determining similarity of elements, and is preferably performed each time a group is updated to include an additional medication. Of course, any other schedule may be provided, including performing the comparison based upon time or after a certain number of new images have been processed. In an alternative embodiment of the invention, the proper combination and grouping of images may also be determined by a measure of similarity between sets of images or by a clustering algorithm applied to the entire collection of images at one single time. For this purpose, a similarity function is preferably applied to two images and outputs a measure of similarity. A preferable similarity function for use in this context is one that emphasizes differences between relevant features such as the medication's shape or color, and also suppress differences which are not relevant to the grouping process such as the influence of lighting conditions or the pose of the medication. In such a manner, the system may make a comparison between all images (or some subset of images) so that the images may be properly grouped according to similarity of differentiating characteristics.

The similarity function may be computed by measuring distance (such as Euclidean) between features describing each pair of images in a group of images (so that the comparison may be made between all pairs of images in a group, or upon some subset of images in the group). Examples of features include color measurements (in the appropriate color space such as L*a*b), or texture features or edge features. These features are preferably extracted and aggregated from different parts of the image. Another approach is to use learned features, this can be done by training a neural network to minimize an appropriate objective (such as the so-called contrastive-loss) on an appropriate dataset of labeled examples. A relevant dataset in this context would be a set of images which are related and for which the ground truth partitioning is known (for example, images of other medications whose identity is already known). In some implementations, images may be characterized as "similar" when the similarity function satisfies a similarity condition. For example, in some implementations, similarity between images may be satisfied when the similarity function exceeds (or fails to reach) a predetermined value. Alternatively, or in addition, similarity between images may be determined based on a comparison to similarity functions for other image pairs or groups of images. For example, in some implementations, similarity between images may be satisfied when the similarity function associated with the images corresponds to the highest value, to one of the two highest values, to one of the three highest values, to one of the four highest values, or to one of the five highest values relative to the similarity function associated with other selected image comparisons. Though greater similarity is expressed above as being associated with higher similarity function values, greater similarity between images may be represented using other scales. For instance, in some implementations, an increasing similarity may be associated with lower similarity function values. Furthermore, a similarity function between one or more images may include a single value (e.g., representative of the similarity between a single corresponding feature in each of the images) or may include multiple values (e.g., representative of the similarity between multiple corresponding features in each of the images).

The preferred similarity function may be learned from previously-collected data. To learn the similarity function, one may use data that has been collected from prior use of the system, even if these uses employed different medications. The learning process can identify what the distinguishing features are, what the features are that contribute less to differentiation between images (as noted above) and how to combine them to measure similarity. A good learned similarity function will preferably generalize to the new medication.

Once discovered, groups that are determined to be similar enough to be merged (see paragraph 32 above) are preferably merged into a single group 142. This is desirable so that initial images of medication that turn out to be outliers in their group do not ultimately cause the groups to remain separate, thus confusing the grouping process.

In accordance with an alternative embodiment of the invention, rather than simply grouping medications presented by a single user, it is possible to group medications provided by multiple users, thus more quickly reaching the time where a sufficient number of medications have been imaged to properly train the system, and move to the second medication recognition phase. Such grouping may be particularly useful when all users a presumably administering the same medication, so that it is likely that the medications are all the same. Still, in the event that more than one medication is to be administered by one or more users, the pooling of image data will allow the separation of images for these groups, and for the accumulation of enough images to properly train the system to properly recognize medication from each of these groups.

In accordance with yet another embodiment of the invention, the user may be provided with a different medication from a healthcare provider or other medication provider. In such a situation, it may be possible to allow the healthcare provider to indicate to the system that the medication has changed, by indicating to the system that the user will be switching medications, preferably in the presence of an individual who can confirm that the medication or object is the expected medication or object, or in accordance with another acceptable method for confirming that the presented medication or object is the correct medication or object, such as through application of a bar code, label, or other identifying characteristic a new particular medication. In this manner, the system is prepared to receive a new medication, and can compare to previously imaged medications, and also confirm that it is not expected that the next medication will necessarily be in the same group as the prior medication. As noted, this indication may be able to allow the medication to be properly grouped without relying solely on the visual characteristics of the images of the medication in order to properly group the medication.

Therefore, the system and method in accordance with the present invention preferably encourages the user to present sequentially "next to be taken" medication or other objects to an imaging device, where still or video images of the medication or object are captured. An initial determination is made as to whether the system is able to confirm that the newly-captured image includes a medication or other object that is the same as that in the base medication or object, or is a different medication. In accordance with embodiments of the invention, the base medication or object may be modified by one or more transfer functions, to account for possible changes in ambient light, etc., to confirm it the newly presented medication or object is the same as the base medication or object.

If it is determined that the newly imaged medication or object is not the same as the base medication or object, an alert may be provided to the user, or to a healthcare provider that the incorrect medication has been presented. To the user, such alert may comprise a notice to the user that the medication is incorrect, and a presentation of further instructions for the user to present the proper medication. Or, the user may be encouraged to confirm that the medication is in fact a new medication to be imaged, such as when a generic medication is provided by another manufacturer, resulting in a different look for the medication that has the same medicinal effect. If it is determined that the newly imaged medication or object is the same as the base medication or object, the user may then be prompted to next administer or ingest the medication. Additionally, the images or video of the newly imaged medication or object is preferably grouped with the base medication, thus expanding the number of samples of the base medication available for use in confirming the proper identity of future imaged medication or objects.

In accordance with a preferred embodiment of the present invention, the described process may continue until a predetermined number of confirmed imaged medications or objects are collected, or until some other measure of a sufficient number of images having been collected is confirmed, such as by testing whether the collected images cover a sufficient number of lighting scenarios, for example.

Once a sufficiently large collection of verified images has been collected it is possible to benchmark generalization. The verified images (positive examples) are preferably partitioned into training, validation and test sets. Negative examples may also be added (comprising images which are known to be different from the current medication). Supervised learning techniques may then be used to train a model with the training and validation sets. The trained model is measured by performance on the test set. This performance (test accuracy) is representative of the learned model's ability to generalize. The crucial detail here is that the test set is sufficiently rich and is representative of the variation in appearances expected during live use.

Once confirmed, the collected images may be processed through a visual learning system, such as through a supervised or unsupervised learning system, to provide a more robust model of the base medication, thus providing an enhanced recognition platform for the future recognition of medication or other objects. This process may be completed multiple times, as increased numbers of collected images, when processed as part of a learning system, will improve the accuracy of the system.

The learning systems preferably focus on a number of consistently-recognizable characteristics of the medication or object. These characteristics may be defined in any number of dimensions, and may include color, shape, surface reflectivity, surface markings, relationship between any number of these characteristics, etc.

Various medications or objects may then be trained so that the system is adapted to recognize and differentiate between these various medications or objects. Once trained, if a user is prescribed one of the trained medications, the system will recognize whether the user presents the prescribed medication to the system (as noted in one or more of the above-note applications). If, however, a medication is prescribed that has not been trained into the system, or if the user is to take a generic medication having a yet unknown set of visual characteristics, the noted process may be employed to allow the system to operate in the absence of any prior training of the particular medication or object.

Figure 5:
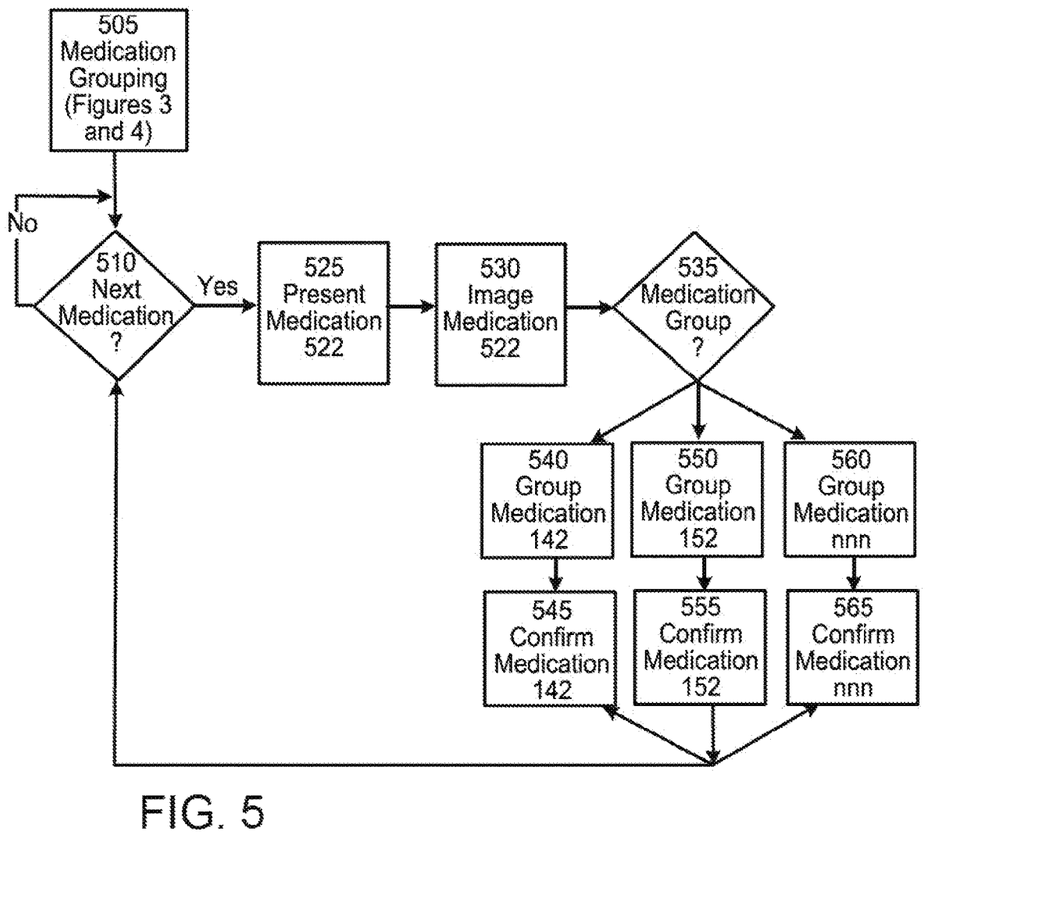
FIG. 5 is a flowchart diagram depicting a method for utilizing a visual system to properly recognize a medication or other object in accordance with an embodiment of the invention.

Therefore, as is shown in FIG. 5, the processes depicted in both FIGS. 3 and 4 are performed for a predetermined period of time, and completed in accordance with the manner described above. These processes are represented in FIG. 5 at step 505. Once these processes 505 are complete, processing then passes to step 510, where it is determined whether a next medication 507 (or other object) is to be presented to the system. If the inquiry at step 510 is answered in the negative, and no medication is to be currently presented to the system, processing returns to step 510 waiting for a next medication to be presented.

If, on the other hand, the inquiry at step 510 is answered in the affirmative, and it is determined that a next medication is to be presented to the system, processing then passes to step 525 where the new medication 522 is presented to the system. Processing preferably continues at step 530 and the system images the medication in accordance with one or more of the methods described in accordance with this invention. Processing then preferably passes to step 535 where a determination is made as to whether the presented medication is confirmed to be part of one or more of the previously determined medication groups 142, 152, nnn in accordance with one or more methods described in accordance with this invention. In this particular embodiment of the invention, no one medication group is designated as an expected medication group, and therefore step 535 makes a determination of whether the newly-imaged medication 522 fits within any of the noted medication groups 142, 152, nnn at corresponding steps 540, 550, 560. Once determined, medication 522 is confirmed as belonging in the proper corresponding group 142, 152, nnn at one of steps 545, 555, 565.

It is possible that medication 522 may appear to fit within more than one of the groups 142, 152, nnn. In other words, the medication may appear to have a "distance" to the medication characteristics in more than one group that is less than a predetermined or calculated threshold amount for recognizing that the medication fits within that group. In such a situation, it may be desirable to determine which group provides the absolute shortest distance and associate the medication 522 with that group. Alternatively, it may be possible to also retain information related to the second best grouping. In this manner, in the future and after additional medication imaging and system training, the composition of the groups changes, the medication 522 can be quickly compared to that previously second best group to determine whether the distance to that group is now the shortest, and that the medication should be regrouped.

Once the medication has been properly grouped and confirmed in one of steps 545, 555, 565, processing preferably returns to step 510 where the system preferably checks at to whether there is a next medication to be presented to the system. As noted above, the comparison of the medication 522 to the multiple groups may be performed in a linear comparison (presented medication 522 being compared to each "N" group independently, resulting in N comparisons), or a hierarchical structure may be determined based upon the determined characteristics of the multiple medication groups 142, 152, nnn (such as a binary tree, for example) resulting in a more efficient searching process). To facilitate efficient search for a query image's nearest neighbor, (and avoid a linear number of comparisons) more efficient data structures, such as KD-trees of Locality Sensitive Hashing, may be employed. As is the case with many image retrieval systems, in this application one can also trade-off exact nearest neighbor search for approximate nearest neighbor search to make significant gains in search efficiency.

In addition, the system preferably learns information from all of the images, irrespective of the group in which the medications are grouped. For example, when imaging medication, various occlusions may be present in one or more of the images. Because the system may rely more heavily on color of the medication, for example, the system may be trained to recognize that the dimension of color is the most critical, while the dimension of shape (which may appear different in accordance with an occlusion) is less critical. As described above with reference to similarity functions, and determination of features more critical to differentiating between medications, the system can learn which characteristics are best able to provide cohesion among similar items, while providing the greatest difference between different items. This is known as improving the quality of distance measuring, essentially more heavily weighting distances determined for dimensions that are most likely to support similarities or distances, while less heavily weighting distances determined for dimensions less likely to support similarities or differences between items. In essence, the system preferably determines which characteristics are most important to making grouping decisions, and which characteristics are less important in making such grouping decisions.

In addition to being applicable to pill-based medications, other medications or medical devices may also be recognized. For example, liquid medications may be imaged, and grouped in a similar manner. With liquid medication, the inventors have determined that color is likely to be a very important dimension, while shape and occlusion are likely to not be as important dimensions. Furthermore, if the liquid medication can be presented to the system in a consistent vessel (such as may be identified by a barcode, label, or other markings on the vessel), then volume or amount of the liquid may also be determined. In such a situation, the inventors of the present invention have determined that shape and size of the liquid volume may be a more important dimension to be measured.

In an additional embodiment of the invention, the system is preferably adapted to rely on medication images from an external database, such as when a medication can be determined based upon recognition of a bar code, label, or other identifying characteristic. In such a manner, once the expected medication is determined from these or other reliable sources, the system preferably accesses one or more external medication databases in order to incorporate images of the medication corresponding to the noted identifying characteristics. These images may then be incorporated into the identified group corresponding to the indicated medication. Alternatively, the images may be compared to images already included in the grouped, imaged medications, and if a match is determined, the imaged medications may be combined, and also identified as belonging to the group indicated by the external database. In such a manner, imaged medications may be identified. Of course, to the extent medications look similar, other identifying characteristics may be employed in order to make a unique determination of medication type.

While the invention has been described making reference to medication, it is equally applicable to any items that are to be visually recognized by a system that does not possess a prior knowledge of the items to be imaged. And, while the system is described employing a data capture and transfer system such as that depicted in FIGS. 1 and 2, the invention is equally applicable to systems employing completely local processing (all processing on a local device without transfer of information to a remote location for processing), or to a cloud or other remote processing scheme, where only image capture is performed at the local location by the local device.

In addition to simply imaging the medication or object during use of the system by a standard user, the user may instead be asked to perform a mini-training process with the system. The user may be asked to show the medication or object to an imaging camera of the system in a predetermined sequence. The user may also be asked to perform a particular gesture or set of gestures or predetermined steps with the medication. The system may turn on lights, or provide illumination from the display of the imaging device, etc. at different times of the mini-training process. Such lights or other illumination may be employed to change the illumination of a medication or environment, or may be used to change a color of the environment, either alone or in sequence, to aid in a more accurate calibration and/or identification process. Use of such a mini-training process increases the number of images available for use as the "base medication" and allows for faster training of the system.

All or part of the processes described herein and their various modifications (hereinafter referred to as "the processes") can be implemented, at least in part, via a computer program product, i.e., a computer program tangibly embodied in one or more tangible, physical hardware storage devices that are computer and/or machine-readable storage devices for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing the processes can be performed by one or more programmable processors executing one or more computer programs to perform the functions of the calibration process. All or part of the processes can be implemented as, special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks. Processors "configured" to perform one or more of the processes, algorithms, functions, and/or steps disclosed herein include one or more general or special purpose processors as described herein as well as one or more computer and/or machine-readable storage devices on which computer programs for performing the processes are stored.

Tangible, physical hardware storage devices that are suitable for embodying computer program instructions and data include all forms of non-volatile storage, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks and volatile computer memory, e.g., RAM such as static and dynamic RAM, as well as erasable memory, e.g., flash memory.

In addition, the logic flows depicted in the figures do not require the particular order shown, or sequential order, to achieve desirable results. In addition, other actions may be provided, or actions may be eliminated, from the described flows, and other components may be added to, or removed from, the described systems. Likewise, actions depicted in the figures may be performed by different entities or consolidated. Furthermore, various separate elements may be combined into one or more individual elements to perform the functions described herein.

Other implementations not specifically described herein are also within the scope of the following claims.

It should be noted that any of the above-noted inventions may be provided in combination or individually. Elements of different embodiments described herein may be combined to form other embodiments not specifically set forth above. Elements may be left out of the processes, computer programs, etc. described herein without adversely affecting their operation. Furthermore, the system may be employed in mobile devices, computing devices, cloud based storage and processing. Camera images may be acquired by an associated camera, or an independent camera situated at a remote location. Processing may be similarly be provided locally on a mobile device, or a remotely at a cloud-based location, or other remote location. Additionally, such processing and storage locations may be situated at a similar location, or at remote locations.

What is claimed:

1. A system, comprising
an imaging apparatus;
a display;
a processor; and
a memory storing instructions that, when executed by the processor, cause the processor to perform operations comprising:
receiving a captured image of an object from the imaging apparatus;
deriving a similarity between one or more characteristics of the captured image and one or more corresponding characteristics of a group of images based on a similarity function, wherein the group of images comprises images of previously imaged objects;
determining that the similarity satisfies a similarity condition;
in response to determining that the similarity satisfies the similarity condition, adding the captured image of the object to the group of images;
determining that a measure of variation in a visual characteristic among the group of images satisfies a condition; and
in response to determining that the measure of variation satisfies the condition, training a supervised or unsupervised visual learning system to recognize a type of the object based on the group of images.

2. The system of claim 1, wherein the object comprises a medication pill.

3. The system of claim 1, wherein the object comprises a medication liquid.

4. The system of claim 1, wherein the object comprises a medical device.

5. The system of claim 1, wherein the operations comprise causing the imaging apparatus to capture one or more further images of an identifier on a vessel associated with the object, wherein the identifier is associated with the group of images.

6. The system of claim 5, wherein the operations comprise retrieving one or more images associated with the identifier from a remote data storage location.

7. The system of claim 1, wherein the measure of variation in the visual characteristic comprises a measure of variation in lighting.

8. The system of claim 1, wherein the one or more characteristics comprise one or more of color, shape, surface reflectivity, or surface markings.

9. The system of claim 8, wherein the one or more characteristics comprise color and at least one other characteristic, and wherein deriving the similarity comprises weighting color more heavily than at least one other characteristic when deriving the similarity.

10. The system of claim 1, wherein the condition comprises that a number of scenarios for the visual characteristic that are portrayed in the group of images is at least a threshold value.

11. A method of training a system to recognize an object, comprising:
presenting a first object to an imaging system;
capturing an image of the first object by the imaging system;
storing the image of the first object in a first group of images;
determining that a measure of variation in a visual characteristic among the first group of images does not satisfy a condition;
until it is determined that the measure of variation satisfies the condition,
obtaining an image of an additional object,
testing whether the image of the additional object satisfies a similarity condition with images in an existing group of images, wherein the similarity condition is based on one or more dimensions of image characteristics,
obtaining, as a result of the testing of the image of the additional object, a determination of whether the image of the additional object satisfies the similarity condition with images in an existing group of images, and
in response to determining that the image of the additional object satisfies the similarity condition with images in the existing group of images, grouping the image of the additional object into the existing group of images for which the similarity condition is satisfied, or
in response to determining that the image of the additional object does not satisfy the similarity condition with images in any existing group of images, grouping the image of the additional object into a new group of images distinct from existing groups of images;

determining that the measure of variation satisfies the condition; and in response to determining that the measure of variation satisfies the condition, training a supervised or unsupervised visual learning system to recognize a type of the first object based on the first group of images.

12. The method of claim 11, further comprising, subsequent to training the supervised or unsupervised visual learning system, presenting a third object to the imaging system;

capturing an image of the third object by the imaging system; and determining, by the supervised or unsupervised visual learning system, whether a type of the third object is the type of the first object.

13. The method of claim 11, wherein the first object is a medication pill.

14. The method of claim 11, wherein the first object is a medication liquid.

15. The method of claim 11, wherein the first object is a medical device.

16. The method of claim 11, wherein the measure of variation in the visual characteristic comprises a measure of variation in lighting.

17. The method of claim 11, wherein the one or more dimensions comprise one or more of color, shape, surface reflectivity, or surface markings.

18. The method of claim 17, wherein the one or more dimensions comprise color and at least one other dimension, and wherein color is weighted more heavily than the at least one other dimension for testing of whether the similarity condition is satisfied.

19. The method of claim 11, wherein the condition comprises that a number of scenarios for the visual characteristic that are portrayed in the first group of images is at least a threshold value.

* * * * *